(12) United States Patent
Zhang et al.

(10) Patent No.: US 10,047,058 B2
(45) Date of Patent: Aug. 14, 2018

(54) COMPOUNDS AND METHODS FOR INHIBITING VACUOLAR ATPASE

(71) Applicants: Chao Zhang, Monterey Park, CA (US); Ying-Chu Chen, Los Angeles, CA (US)

(72) Inventors: Chao Zhang, Monterey Park, CA (US); Ying-Chu Chen, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/384,016

(22) Filed: Dec. 19, 2016

(65) Prior Publication Data

US 2017/0174638 A1  Jun. 22, 2017

Related U.S. Application Data

(60) Provisional application No. 62/269,739, filed on Dec. 18, 2015.

(51) Int. Cl.
*C07D 239/94* (2006.01)
(52) U.S. Cl.
CPC .................... *C07D 239/94* (2013.01)
(58) Field of Classification Search
CPC .................................................... C07D 239/94
See application file for complete search history.

(56) References Cited

FOREIGN PATENT DOCUMENTS

WO   WO2003081210   * 10/2003   ........... C07D 239/93

* cited by examiner

*Primary Examiner* — Paul V Ward
(74) *Attorney, Agent, or Firm* — DLA Piper LLP (US)

(57) ABSTRACT

A compound of Formula II,

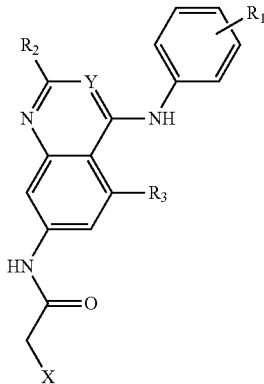

is provided. $R_1$, $R_2$ and $R_3$ are independently either hydrogen, alkyl, aryl, halogen, alkoxy, nitro, amino or hydroxyl. X is either F, Cl, Br, I or CN. Y is either N or CH. Compositions that include Formula II can be used to inhibit vacuolar $H^+$ ATPase.

13 Claims, 12 Drawing Sheets

FIG. 6

| Accession | Description | Probe | | | | Fold Enrichment | MW [kDa] |
|---|---|---|---|---|---|---|---|
| | | Spectral Counts | | Area | | | |
| | | - | + | - | + | | |
| P38606 | V-type proton ATPase catalytic subunit A OS=Homo sapiens GN=ATP6V1A PE=1 SV=2 - [VATA_HUMAN] | 15 | 354 | 1.61E+08 | 6.43E+10 | 398.88 | 68.3 |

COMPOUNDS AND METHODS FOR INHIBITING VACUOLAR ATPASE

CROSS-REFERENCE TO RELATED APPLICATIONS

This application claims priority to U.S. Provisional Application Ser. No. 62/269,739, filed on Dec. 18, 2015, the entire contents of which are incorporated herein by reference in their entirety.

STATEMENT REGARDING FEDERALLY SPONSORED RESEARCH OR DEVELOPMENT

This invention was made with government support under National Science Foundation grant CHE-1455306. The government has certain rights in the invention.

FIELD OF THE INVENTION

The present invention relates to compounds and methods for inhibiting vacuolar ATPase.

BACKGROUND OF THE INVENTION

The pH of the intracellular compartment is tightly controlled in all eukaryotic cells. This control is crucial for various biological processes, including intracellular membrane trafficking, endocytosis, protein degradation, bone resorption, and small-molecule uptake. The vacuolar $H^+$ ATPase (V-ATPase) is one of the central players in regulating acidity in eukaryotic cells and the loss of V-ATPase function is in general lethal at early stages of development.

V-ATPases are large multi-subunit protein complexes that function as a rotary molecular motor, and are organized into two domains, $V_0$ and $V_1$. The $V_1$ domain is located on the cytoplasmic side of the membrane and carries out ATP hydrolysis, whereas the $V_0$ domain is a membrane embedded complex that is responsible for proton translocation across the membrane.[1-3] The $V_1$ domain is composed of eight different subunits (A, B, C, D, E, F, G, H) and the $V_0$ domain contains five different subunits (a, b, c, d, and e) in mammals, some of which are present in multiple copies. The core of the $V_1$ domain contains a hexamer of A and B subunits, which participates in ATP binding and hydrolysis with the most of the residues responsible for ATP binding contributed by the catalytic subunit A.

Dysregulation of V-ATPase has been implicated in a number of diseases, including renal disease (renal tubular acidosis)[4], bone disease (osteoporosis)[5], and tumor metastasis.[6] For example, the V-ATPase activity has been found to be significantly higher in the highly invasive MB231 breast cancer cells than the largely non-metastatic MCF7 cells.[6,7] The treatment of MB231 cells with bafilomycin, a known V-ATPase inhibitor, significantly inhibited the invasiveness of cancer cells, suggesting that V-ATPase is a potential drug target for blocking cancer metastasis.[2,8] In addition to cancer, V-ATPase is also implicated in renal and bone diseases.[2,9]

A number of inhibitors of V-ATPase have been identified and tested for their therapeutic potentials. For example, macrolide antibiotics with 18-membered lactone rings, bafilomycin and concanamycin, were found to be selective inhibitors of V-ATPases soon after their isolation from Streptomyces in the 1980s.[10] A series of studies revealed that these plecomacrolides primary bound to the $V_0$ subunit c and perturbed rotation of the b/c-ring. In addition to inhibiting V-ATPase, bafilomycin impairs mitochondrial function by acting as a carrier type potassium ionophore.[11]

Additional inhibitors of V-ATPase were subsequently discovered,[10] such as archazolid, which is a natural product produced by the myxobacteria Archangium gephyra and Cystobacter violaceus. Archazolid, which also binds to c subunit, appears to be a highly potent V-ATPase inhibitor and blocks the growth of mammalian cells at subnanomolar concentrations. Another class of V-ATPase inhibitors, benzolactone enamides (e.g., salicylihamide, apicularens and cruentaren) that was isolated from various natural sources, demonstrated potent inhibition against mammalian V-ATPase, but surprisingly no effects on fungal V-ATPase. However, these natural products tend to be highly toxic to mammalian cells. Previous studies revealed that the binding sites of benzolactone enamides should still reside within $V_0$ domain but differ from plecomacrolides. A number of novel indole derivatives were synthesized based on bafilomycin structure. Among these indole-containing bafilomycin analogs, INDOL0 interacts with the $V_0$ subunit c and cause potent inhibition against V-ATPase. A number of V-ATPase inhibitors such as synthetic benzolactone enamide RTA203 (a derivative of salicylihalamide), indole derivatives NiK12192 and SB24278, tributyltin chloride (TBTCl), 3-bromopyruvate (3-Br-PA) have been reported recently. However, the binding site of these synthetic V-ATPase inhibitors is often not known. Novel small molecules with defined mechanism of inhibition against V-ATPase are needed to evaluate the therapeutic potential of V-ATPase inhibitors in human diseases.

SUMMARY OF THE INVENTION

One aspect of the present invention is directed to the compound of Formula II.

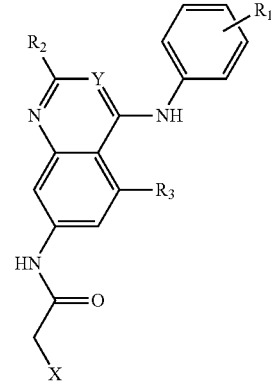

Formula II

In Formula II, $R_1$, $R_2$, and $R_3$ are independently an alkyl, aryl, halogen, alkoxy, nitro, amino or hydroxyl group. X is any halogen or other leaving group such as CN. Y is N or CH. Halogens include F, Cl, Br, and I.

In one embodiment, $R_1$ is hydrogen, $R_2$ is hydrogen, $R_3$ is hydrogen, X is Cl, and Y is N.

In another embodiment, $R_1$ is hydrogen, $R_2$ is hydrogen, $R_3$ is hydrogen, X is F, and Y is N.

In another embodiment, $R_1$ is hydrogen, $R_2$ is hydrogen, $R_3$ is hydrogen, X is Br, and Y is N.

In another embodiment, $R_1$ is hydrogen, $R_2$ is hydrogen, $R_3$ is hydrogen, X is I, and Y is N.

In another embodiment, $R_1$ is hydrogen, $R_2$ is hydrogen, $R_3$ is hydrogen, X is CN, and Y is N.

In another embodiment, $R_1$ is hydrogen, $R_2$ is hydrogen, $R_3$ is hydrogen, X is Cl, and Y is CH.

In another embodiment, $R_1$ is hydrogen, $R_2$ is hydrogen, $R_3$ is hydrogen, X is F, and Y is CH.

In another embodiment, $R_1$ is hydrogen, $R_2$ is hydrogen, $R_3$ is hydrogen, X is Br, and Y is CH.

In another embodiment, $R_1$ is hydrogen, $R_2$ is hydrogen, $R_3$ is hydrogen, X is I, and Y is CH.

In another embodiment, $R_1$ is hydrogen, $R_2$ is hydrogen, $R_3$ is hydrogen, X is CN, and Y is CH.

Another aspect of the present invention is directed to a method of inhibiting vacuolar $H^+$ ATPase. The method includes treating vacuolar $H^+$ ATPase with a composition that includes Formula II. In Formula II, $R_1$, $R_2$, and $R_3$ are independently an alkyl, aryl, halogen, alkoxy, nitro, amino or hydroxyl group. X is any halogen or other leaving group such as CN. Y is N or CH.

In one embodiment of the method of treating vacuolar $H^+$ ATPase with a composition that includes Formula II, $R_1$ is hydrogen, $R_2$ is hydrogen, $R_3$ is hydrogen, X is Cl, and Y is N.

In another embodiment, a catalytic subunit of vacuolar $H^+$ ATPase is targeted.

Other aspects and advantages of the invention will be apparent from the following description and the appended claims.

BRIEF DESCRIPTION OF THE DRAWINGS

FIG. 6. MS analysis revealed the identity of target protein: the catalytic subunit A of vacuolar ATPase. Most possible protein target: V-type proton ATPase catalytic subunit A (ATP6V1A).

DETAILED DESCRIPTION OF THE INVENTION

As used herein, an "alkyl" group can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "aryl" refers to aromatic monocyclic or multicyclic groups containing from 3 to 16 carbon atoms. As used in this specification, aryl groups are aryl radicals which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or an alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used herein, "halogen" refers to F, Cl, Br or I.

As used herein, "alkoxy" refers to RO—, in which R is an alkyl group.

As used herein, "amino" refers to a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

Figure 1:
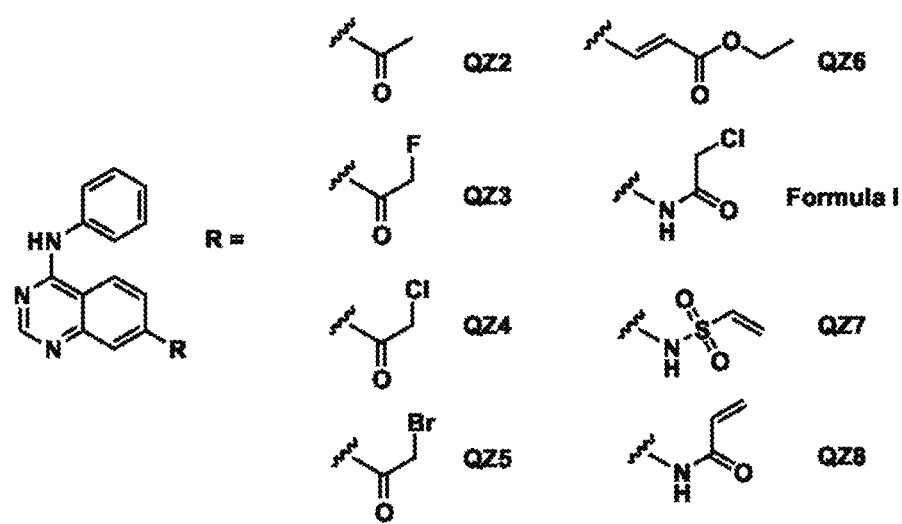
FIG. 1. Structures of electrophilic quinazolines.
Figure 2:
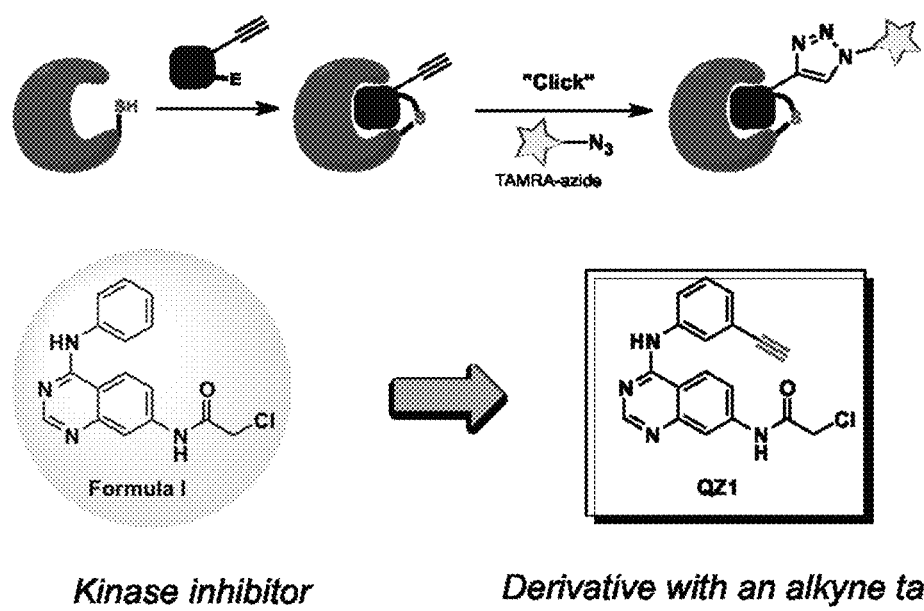
FIG. 2. Attaching an alkyne tag to enable target protein detection by click reaction.
Figure 3:
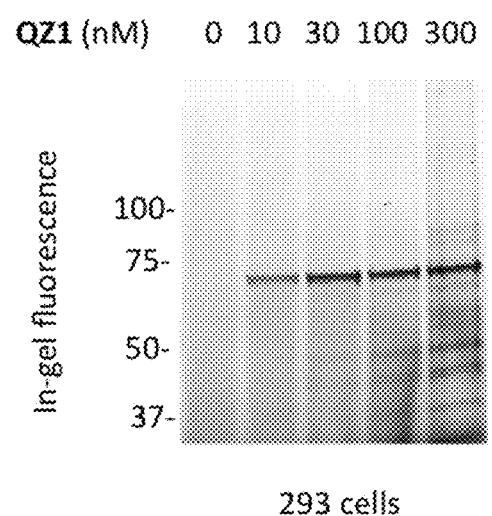
FIG. 3. Specific labeling of a cellular protein by the probe. 293 cells were labeled by probe QZ1 for 30 min, lysed, followed by CuAAC-mediated conjugation with TAMRA-azide and in-gel fluorescence imaging.

All the clinically used inhibitors of epidermal growth factor receptor (EGFR) and Her2, including erlotinib, gefitinib, lapatinib, afatinib, poziotinib and dacomitinib, contain a heterocyclic core of 4-anilinoquinazoline. A series of quinazolines containing electrophiles at the 7 position to achieve covalent inhibition of protein kinases were prepared (FIG. 1). In an effort to monitor the cellular selectivity of these electrophilic quinazolines, one electrophilic quinazoline (Formula I) was derivatized with a terminal alkyne group as a reporter at the 3' position of the anilino group (FIG. 2). Treatment of cells with the resulting small-molecule probe QZ1 followed by cell lysis, CuAAC (Cu(I)-catalyzed [3+2] azide-alkyne cycloaddition) with Tetramethylrhodamine (TAMRA) azide, and SDS-PAGE is expected to reveal proteins covalently labeled with the probe as fluorescent bands in the gel. When the probe was tested on HEK293 cells in this format, only one major fluorescent band in the gel was observed. The protein has an estimated size of 70 kDa and it is selectively labeled by QZ1 at concentrations ranging from 10 nM to 300 nM (FIG. 3).

Formula I

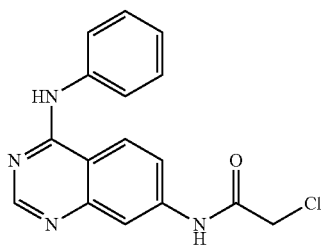

Formula I was synthesized by the inventors as detailed in synthetic Scheme I.

Scheme I

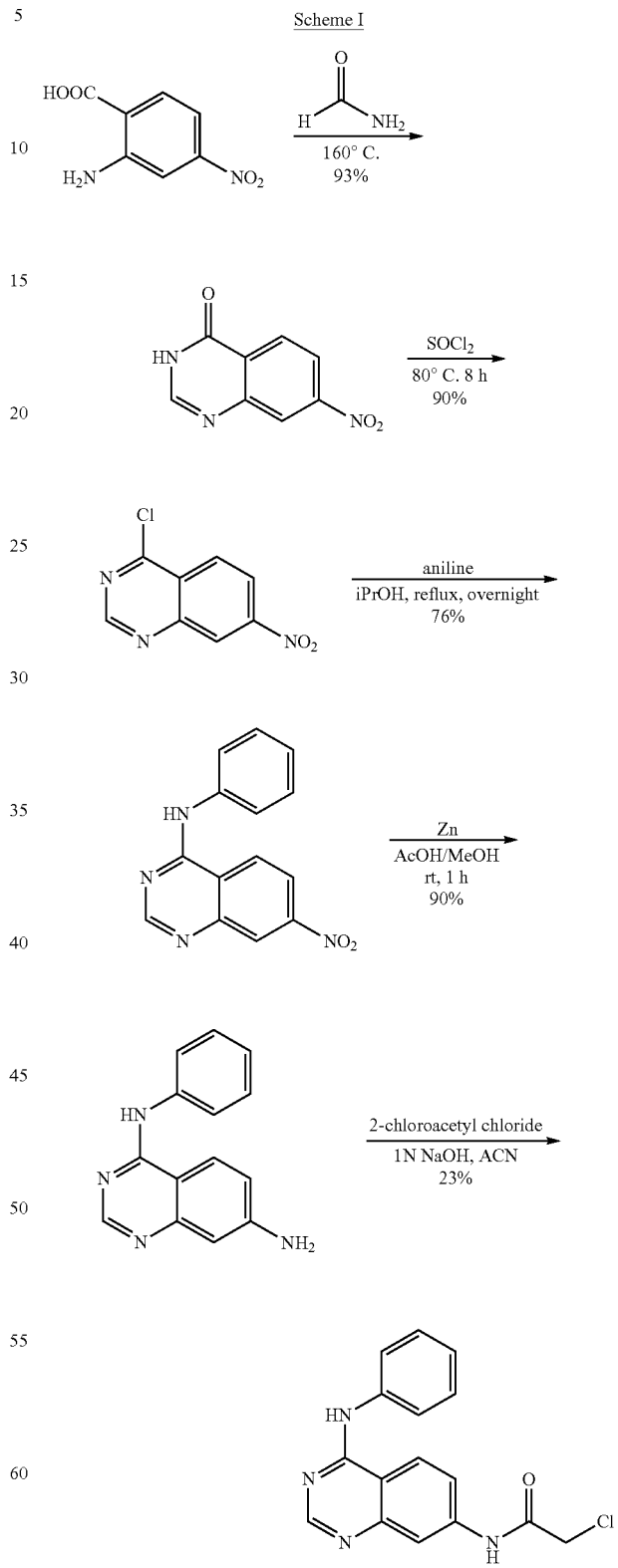

Figure 4:
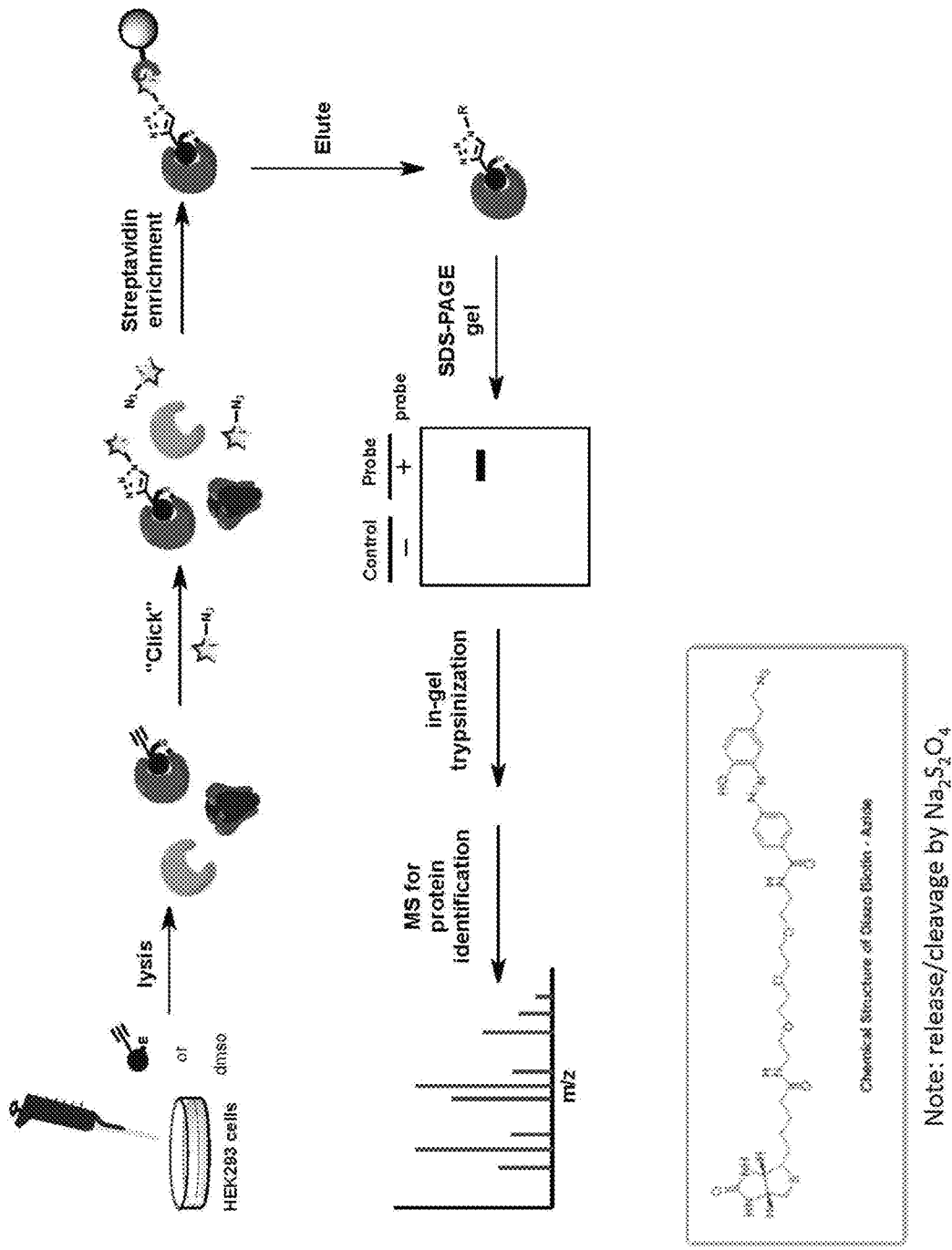
FIG. 4. Schematic procedure for target labelling, pull-down and identification.
Figure 5:
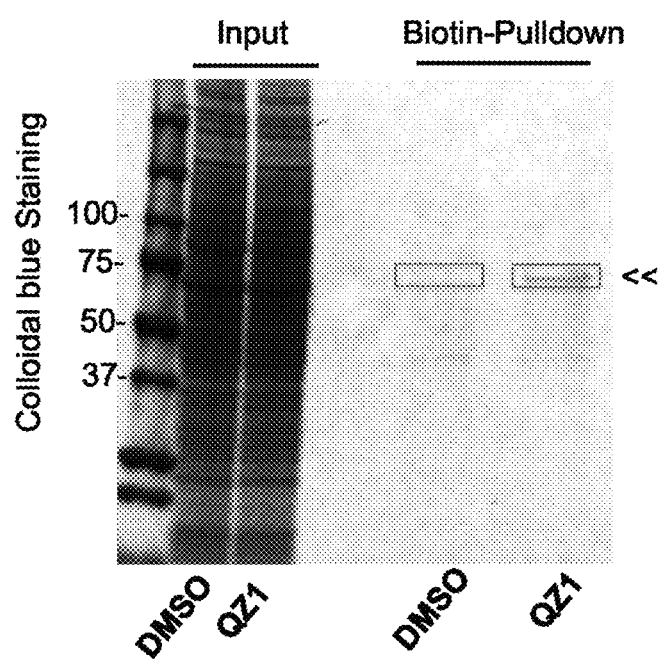
FIG. 5. Streptavidin enrichment. Biotin-pulldown from 10 mg of 293 cell lysate. 30 µL out of 40 µL biotin-pulldown sample was loaded.
Figure 7:
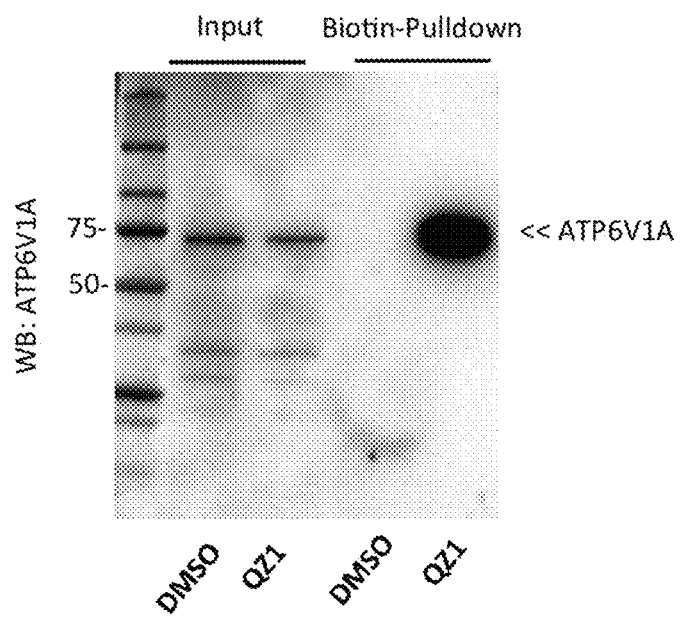
FIG. 7. Western blot confirmed the protein identity. Thirty µg of input was loaded. 2.5 µL out of 40 µL biotin-pulldown sample was loaded. ATP6V1A antibody 1:2000 in 5% BSA.

To identify this protein target, 293 cells were treated with DMSO or 100 nM of probe QZ1 for 30 minutes before being lysed, and cell lysates were reacted with a cleavable biotin-azo-azide under CuAAC. The biotin-linked target proteins were then captured by streptavidin agarose beads, followed by elution, SDS-PAGE, and in-gel trypsinization. The digested-peptide fragments were then analyzed by mass spectrometry (FIGS. 4 and 5). Based on MS analysis, we concluded that the protein labeled by our probe was likely the vacuolar ATPase catalytic subunit A (ATP6V1A) (FIG. 6). Importantly, ATP6V1A has the theoretical size of 68.3 kDa. The results have been further confirmed by western blot analysis using an established ATP6V1A antibody (FIG. 7).

Figure 8:
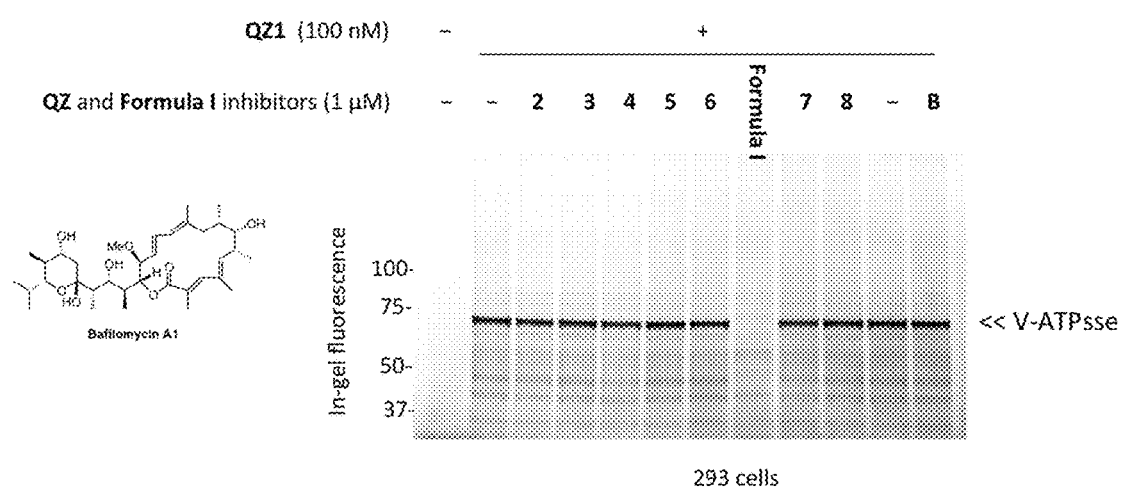
FIG. 8. Screening electrophilic quinazolines for inhibition of labeling (1 µM) by probe QZ1. Cells were pretreated with drug for 30 min before incubation with the probe for another 30 min.
Figure 9:
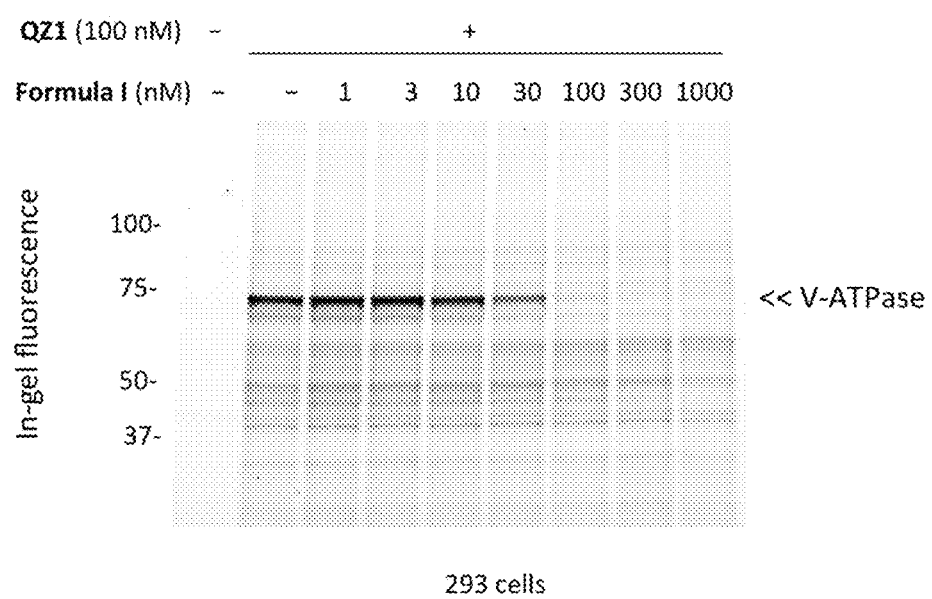
FIG. 9. Potent target engagement by Formula I in cells. Cells were pretreated with Formula I for 30 min before incubation with 100 nM probe for another 30 min.
Figure 10:
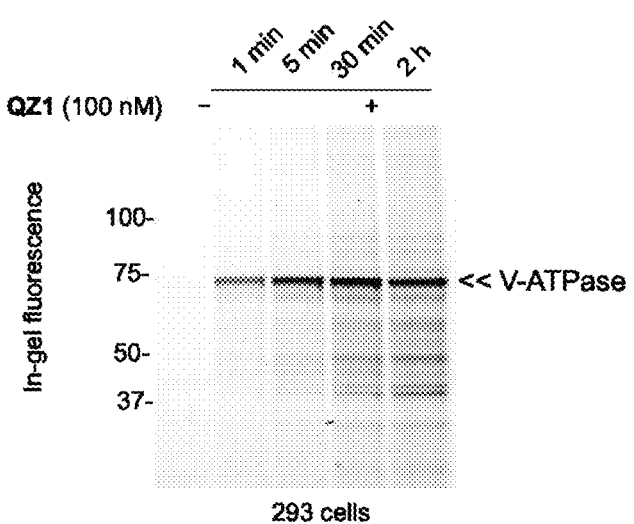
FIG. 10. Rapid target occupancy by the probe QZ1 in cells.
Figure 11:
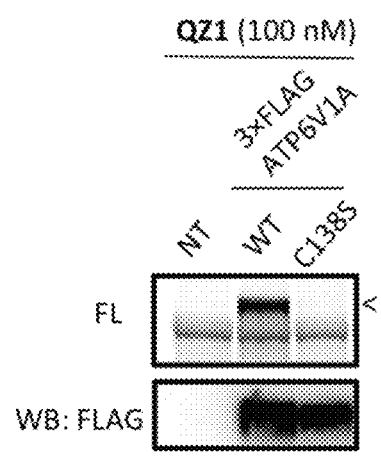
FIG. 11. Identification of probe modification site in ATP6V1A. Top panel is an in-gel fluorescence image and bottom is a western blot.
Figure 12:
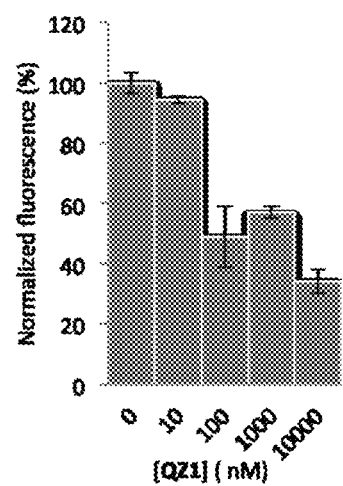
FIG. 12. Effects of QZ1 on V-ATPase re-acidification.

To determine the SAR, a series of electrophilic quinazolines synthesized were screened for ones that can inhibit the probe labeling. Bafilomycin A1, a known V-ATPase inhibitor targeting $V_O$ domain, was included as a control in the screen. Out of this series of electrophilic quinazolines, only Formula I that contains the same chloroacetamide electrophile as the probe QZ1 showed potent inhibition (FIG. 8). These results suggest that chloroacetamide has unique reactivity toward a nucleophilic residue (most likely a cysteine, to be identified) in ATP6V1A. To measure the potency of Formula I at inhibiting ATP6V1A labeling by QZ1, 293 cells were first incubated with Formula I for 30 minutes, and then the cells were washed twice with PBS followed by probe addition. The apparent $IC_{50}$ of Formula I against ATP6V1A labeling by QZ1 is determined to be around 30 nM suggesting that Formula I is a potent and irreversible binder of ATP6V1A (FIG. 9). Furthermore, the time course of ATP6V1A labeling by probe QZ1 was determined. 293 Cells were treated with 100 nM of QZ1 for various lengths of time (ranging from 1 minute to 2 hours). At 5 minutes, intense labeling (close to saturation) of ATPase was observed (FIG. 10). Taken together, these results indicate the potent and rapid target engagement of the V-type ATPase catalytic subunit by Formula I and QZ1 in cells. Furthermore, transfection of 293 cells with 3×FLAG-tagged human ATP6V1A followed by treatment with probe QZ1 led to the appearance of a new labeled band of slightly retarded mobility compared to the original band (FIG. 11, arrow) and mutation of cysteine 138 to serine in ATP6V1A abolished probe labeling, suggesting C138 is the probe QZ1 labeling site (FIG. 11). To test if probe QZ1 affects V-ATPase function, the probe was applied to a pH recovery assay to study V-ATPase inhibition in cells, which involves pre-treatment with bafilomycin and measuring vesicle re-acidification after it has been washed off. Immediately after bafilomycin washout, cells were treated with probe QZ1 at various concentrations, labeled with a fluorescent dye DND-99, followed by lysis and fluorescence measurement after 3 h. Probe QZ1 inhibited vesicle re-acidification with an apparent $IC_{50}$ value of 30 nM (FIG. 12).

Other inhibitors of V-ATPase are represented by the following general formula (Formula II).

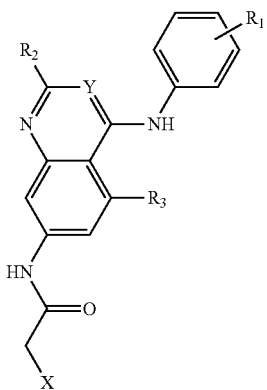

Formula II

In Formula II, $R_1$, $R_2$, and $R_3$ are independently an alkyl, aryl, halogen, alkoxy, nitro, amino or hydroxyl group. X is any halogen or other leaving group such as CN. Y is N or CH.

In accordance with one embodiment of the present invention, a compound of Formula II,

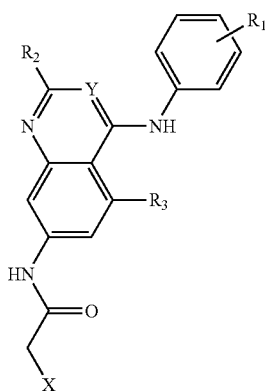

wherein $R_1$ is selected from the group consisting of hydrogen, alkyl, aryl, halogen, alkoxy, nitro, amino and hydroxyl, $R_2$ is selected from the group consisting of hydrogen, alkyl, aryl, halogen, alkoxy, nitro, amino and hydroxyl, $R_3$ is selected from the group consisting of hydrogen, alkyl, aryl, halogen, alkoxy, nitro, amino and hydroxyl, X is selected from the group consisting of F, Cl, Br, I and CN, and Y is N or CH is claimed.

In accordance with another embodiment of the present invention, the compound Formula II, wherein $R_1$ is hydrogen, $R_2$ is hydrogen, $R_3$ is hydrogen, X is Cl, and Y is N is claimed.

In accordance with another embodiment of the present invention, the compound Formula II, wherein $R_1$ is hydrogen, $R_2$ is hydrogen, $R_3$ is hydrogen, X is F, and Y is N is claimed.

In accordance with another embodiment of the present invention, the compound Formula II, wherein $R_1$ is hydrogen, $R_2$ is hydrogen, $R_3$ is hydrogen, X is Br, and Y is N is claimed.

In accordance with another embodiment of the present invention, the compound Formula II, wherein $R_1$ is hydrogen, $R_2$ is hydrogen, $R_3$ is hydrogen, X is I, and Y is N is claimed.

In accordance with another embodiment of the present invention, the compound Formula II, wherein $R_1$ is hydrogen, $R_2$ is hydrogen, $R_3$ is hydrogen, X is CN, and Y is N is claimed.

In accordance with another embodiment of the present invention, the compound Formula II, wherein $R_1$ is hydrogen, $R_2$ is hydrogen, $R_3$ is hydrogen, X is Cl, and Y is CH is claimed.

In accordance with another embodiment of the present invention, the compound Formula II, wherein $R_1$ is hydrogen, $R_2$ is hydrogen, $R_3$ is hydrogen, X is F, and Y is CH is claimed.

In accordance with another embodiment of the present invention, the compound Formula II, wherein $R_1$ is hydrogen, $R_2$ is hydrogen, $R_3$ is hydrogen, X is Br, and Y is CH is claimed.

In accordance with another embodiment of the present invention, the compound Formula II, wherein $R_1$ is hydrogen, $R_2$ is hydrogen, $R_3$ is hydrogen, X is I, and Y is CH is claimed.

In accordance with another embodiment of the present invention, the compound Formula II, wherein $R_1$ is hydrogen, $R_2$ is hydrogen, $R_3$ is hydrogen, X is CN, and Y is CH is claimed.

In accordance with another embodiment of the present invention, a method of inhibiting vacuolar $H^+$ ATPase comprises treating vacuolar $H^+$ ATPase with a composition comprising Formula II, wherein $R_1$ is selected from the group consisting of hydrogen, alkyl, aryl, halogen, alkoxy, nitro, amino and hydroxyl, $R_2$ is selected from the group consisting of hydrogen, alkyl, aryl, halogen, alkoxy, nitro, amino and hydroxyl, $R_3$ is selected from the group consisting of hydrogen, alkyl, aryl, halogen, alkoxy, nitro, amino and hydroxyl, X is selected from the group consisting of F, Cl, Br, I and CN, and Y is N or CH.

In accordance with another embodiment of the present invention, a method of inhibiting vacuolar $H^+$ ATPase comprises treating vacuolar $H^+$ ATPase with a composition comprising Formula II, wherein $R_1$ is hydrogen, $R_2$ is hydrogen, $R_3$ is hydrogen, X is Cl, and Y is N.

In accordance with another embodiment of the present invention, a method of inhibiting vacuolar $H^+$ ATPase comprises treating vacuolar $H^+$ ATPase with a composition comprising Formula II, wherein $R_1$ is selected from the group consisting of hydrogen, alkyl, aryl, halogen, alkoxy, nitro, amino and hydroxyl, $R_2$ is selected from the group consisting of hydrogen, alkyl, aryl, halogen, alkoxy, nitro, amino and hydroxyl, $R_3$ is selected from the group consisting of hydrogen, alkyl, aryl, halogen, alkoxy, nitro, amino and hydroxyl, X is selected from the group consisting of F, Cl, Br, I and CN, and Y is N or CH, wherein a catalytic subunit A of the vacuolar $H^+$ ATPase is targeted.

In accordance with another embodiment of the present invention, a method of inhibiting vacuolar $H^+$ ATPase comprises treating vacuolar $H^+$ ATPase with a composition comprising Formula II, wherein $R_1$ is hydrogen, $R_2$ is hydrogen, $R_3$ is hydrogen, X is Cl, and Y is N, wherein a catalytic subunit A of the vacuolar $H^+$ ATPase is targeted.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.
1. Beyenbach, K. W.; Wieczorek, H. *J Exp Biol* 2006, 209, 577-589.
2. Forgac, M. *Nat Rev Mol Cell Bio* 2007, 8, 917-929.
3. Maxson, M. E.; Grinstein, S. *J Cell Sci* 2014, 127, 4987-4993.
4. Karet, F. E.; Finberg, K. E.; Nelson, R. D.; Nayir, A.; Mocan, H.; Sanjad, S. A.; Rodriguez-Soriano, J.; Santos, F.; Cremers, C. W. R. J.; Di Pietro, A.; Hoffbrand, B. I.; Winiarski, J.; Bakkaloglu, A.; Ozen, S.; Dusunsel, R.; Goodyer, P.; Hulton, S. A.; Wu, D. K.; Skvorak, A. B.; Morton, C. C.; Cunningham, M. J.; Jha, V.; Lifton, R. P. *Nat Genet* 1999, 21, 84-90.
5. Toyomura, T.; Murata, Y.; Yamamoto, A.; Oka, T.; Sun-Wada, G. H.; Wada, Y.; Futai, M. *Journal of Biological Chemistry* 2003, 278, 22023-22030.
6. Sennoune, S. R.; Bakunts, K.; Martinez, G. M.; Chua-Tuan, J. L.; Kebir, Y.; Attaya, M. N.; Martinez-Zaguilan, R. *Am J Physiol-Cell Ph* 2004, 286, C1443-C1452.
7. Hinton, A.; Sennoune, S. R.; Bond, S.; Fang, M.; Reuveni, M.; Sahagian, G. G.; Jay, D.; Martinez-Zaguilan, R.; Forgac, M. *Journal of Biological Chemistry* 2009, 284, 16400-16408.
8. Perez-Sayans, M.; Somoza-Martin, J. M.; Barros-Angueira, F.; Rey, J. M.; Garcia-Garcia, A. *Cancer Treat Rev* 2009, 35, 707-713.
9. Qin, A.; Cheng, T. S.; Pavlos, N. J.; Lin, Z.; Dai, K. R.; Zheng, M. H. *Int J Biochem Cell B* 2012, 44, 1422-1435.
10. Huss, M.; Wieczorek, H. *J Exp Biol* 2009, 212, 341-346.
11. Teplova, V. V.; Tonshin, A. A.; Grigoriev, P. A.; Saris, N. E. L.; Salkinoja-Salonen, M. S. *J Bioenerg Biomembr* 2007, 39, 321-329.

What is claimed is:

1. A compound of Formula II,

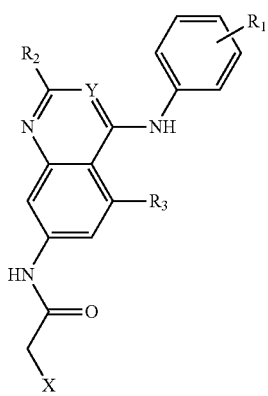

wherein $R_1$ is selected from the group consisting of hydrogen, alkyl, aryl, halogen, alkoxy, nitro, amino and hydroxyl, $R_2$ is selected from the group consisting of hydrogen, alkyl, aryl, halogen, alkoxy, nitro, amino and hydroxyl, $R_3$ is selected from the group consisting of hydrogen, alkyl, aryl, halogen, alkoxy, nitro, amino and hydroxyl, X is selected from the group consisting of F, Br, I and CN, and Y is N or CH.

2. The compound of claim 1, wherein $R_1$ is hydrogen, $R_2$ is hydrogen, $R_3$ is hydrogen, X is F, and Y is N.

3. The compound of claim 1, wherein $R_1$ is hydrogen, $R_2$ is hydrogen, $R_3$ is hydrogen, X is Br, and Y is N.

4. The compound of claim 1, wherein $R_1$ is hydrogen, $R_2$ is hydrogen, $R_3$ is hydrogen, X is I, and Y is N.

5. The compound of claim 1, wherein $R_1$ is hydrogen, $R_2$ is hydrogen, $R_3$ is hydrogen, X is CN, and Y is N.

6. The compound of claim 1, wherein $R_1$ is hydrogen, $R_2$ is hydrogen, $R_3$ is hydrogen, X is F, and Y is CH.

7. The compound of claim 1, wherein $R_1$ is hydrogen, $R_2$ is hydrogen, $R_3$ is hydrogen, X is Br, and Y is CH.

8. The compound of claim 1, wherein $R_1$ is hydrogen, $R_2$ is hydrogen, $R_3$ is hydrogen, X is I, and Y is CH.

9. The compound of claim 1, wherein $R_1$ is hydrogen, $R_2$ is hydrogen, $R_3$ is hydrogen, X is CN, and Y is CH.

10. A method of inhibiting vacuolar $H^+$ ATPase comprising treating vacuolar $H^+$ ATPase with a composition comprising a compound of Formula II,

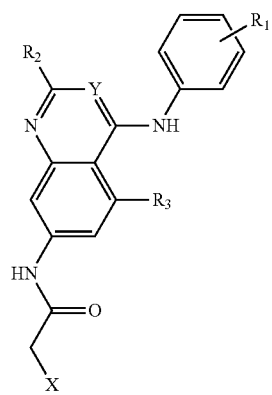

wherein $R_1$ is selected from the group consisting of hydrogen, alkyl, aryl, halogen, alkoxy, nitro, amino and hydroxyl, $R_2$ is selected from the group consisting of hydrogen, alkyl, aryl, halogen, alkoxy, nitro, amino and hydroxyl, $R_3$ is selected from the group consisting of hydrogen, alkyl, aryl, halogen, alkoxy, nitro, amino and hydroxyl, X is selected from the group consisting of F, Cl, Br, I and CN, and Y is N or CH.

11. A method of inhibiting vacuolar $H^+$ ATPase comprising treating vacuolar $H^+$ ATPase with a composition comprising the compound of claim 10, wherein $R_1$ is hydrogen, $R_2$ is hydrogen, $R_3$ is hydrogen, X is Cl, and Y is N.

12. The method of claim 10, wherein a catalytic subunit A of the vacuolar $H^+$ATPase is targeted.

13. The method of claim 11, wherein a catalytic subunit A of the vacuolar $H^+$ATPase is targeted.

* * * * *